(12) United States Patent
Kim

(10) Patent No.: US 10,973,576 B2
(45) Date of Patent: Apr. 13, 2021

(54) OPTICAL TREATMENT APPARATUS AND CONTROL METHOD THEREFOR

(71) Applicant: LUTRONIC CORPORATION, Goyang (KR)

(72) Inventor: Jong Min Kim, Seoul (KR)

(73) Assignee: LUTRONIC CORPORATION, Goyang (KR)

( * ) Notice: Subject to any disclaimer, the term of this patent is extended or adjusted under 35 U.S.C. 154(b) by 170 days.

(21) Appl. No.: 15/754,908

(22) PCT Filed: Aug. 25, 2015

(86) PCT No.: PCT/KR2015/008893
§ 371 (c)(1),
(2) Date: Feb. 23, 2018

(87) PCT Pub. No.: WO2017/034048
PCT Pub. Date: Mar. 2, 2017

(65) Prior Publication Data
US 2018/0263695 A1 Sep. 20, 2018

(30) Foreign Application Priority Data
Aug. 24, 2015 (KR) .......................... 10-2015-0118981

(51) Int. Cl.
*A61F 9/008* (2006.01)
*A61F 9/007* (2006.01)
(Continued)

(52) U.S. Cl.
CPC ................ *A61B 18/20* (2013.01); *A61B 5/00* (2013.01); *A61B 5/0066* (2013.01); *A61B 5/01* (2013.01);
(Continued)

(58) Field of Classification Search
CPC ......... A61B 18/20; A61B 5/01; A61B 5/0066; A61B 5/0036; A61B 5/4836; A61F 9/008;
(Continued)

(56) References Cited

U.S. PATENT DOCUMENTS

2003/0032949 A1 2/2003 Schuele et al.
2004/0098070 A1* 5/2004 Mohr ..................... A61B 18/20
607/89

(Continued)

FOREIGN PATENT DOCUMENTS

EP 3192478 A1 7/2017
JP 2002-518122 A 6/2002
(Continued)

OTHER PUBLICATIONS

International Search Report for International Patent Application No. PCT/KR2015/008893, filed on Aug. 25, 2015.
(Continued)

*Primary Examiner* — Allen Porter
*Assistant Examiner* — Adreanne A. Arnold

(57) ABSTRACT

The present invention relates to an optical treatment apparatus and an operating method thereof. The present invention provides an optical treatment apparatus and an operating method thereof, the optical treatment apparatus comprising: a treatment beam generation unit for generating a treatment beam; a beam delivery unit for forming a path through which the treatment beam generated from the treatment beam generation unit travels to a treatment area located in a fundus; a monitoring unit for irradiating a detecting beam along the path through which the treatment beam travels, and detecting state information on the treatment area on the basis of speckle change information of the detecting beam scattered and reflected from the treatment area; and a control unit for controlling the driving of the treatment beam (Continued)

generation unit on the basis of the state information on the treatment area detected by the monitoring unit.

16 Claims, 13 Drawing Sheets

(51) Int. Cl.
    *A61B 5/00* (2006.01)
    *A61B 18/20* (2006.01)
    *A61N 5/06* (2006.01)
    *A61B 5/01* (2006.01)
    *G01K 13/00* (2021.01)

(52) U.S. Cl.
    CPC ............ *A61B 5/4836* (2013.01); *A61F 9/007* (2013.01); *A61F 9/008* (2013.01); *A61N 5/06* (2013.01); *A61F 2009/00851* (2013.01); *A61F 2009/00861* (2013.01); *A61F 2009/00863* (2013.01); *G01K 13/002* (2013.01)

(58) Field of Classification Search
    CPC . A61F 2009/00851; A61F 2009/00863; A61N 5/06
    See application file for complete search history.

(56) References Cited

U.S. PATENT DOCUMENTS

| | | | |
|---|---|---|---|
| 2006/0233216 A1* | 10/2006 | Schuele | G01J 5/0022 374/130 |
| 2009/0177094 A1* | 7/2009 | Brown | A61B 5/0066 600/476 |
| 2009/0318908 A1 | 12/2009 | Van Pieterson et al. | |
| 2011/0270092 A1 | 11/2011 | Kang et al. | |
| 2015/0121276 A1 | 4/2015 | Ryu et al. | |
| 2015/0366705 A1 | 12/2015 | Ha et al. | |

FOREIGN PATENT DOCUMENTS

| | | |
|---|---|---|
| JP | 2013-504394 A | 2/2013 |
| JP | 2014-150889 A | 8/2014 |
| KR | 10-2009-0027200 A | 3/2009 |
| KR | 10-1172745 B1 | 8/2012 |
| KR | 10-2014-0009846 A | 1/2014 |
| KR | 10-2015-0047935 A | 5/2015 |
| WO | 9966835 A1 | 12/1999 |
| WO | WO2015088226 A1 | 6/2015 |

OTHER PUBLICATIONS

European Search Report issued in related EP Application No. 15902320.9 dated Mar. 27, 2019, 9 pages.

* cited by examiner

OPTICAL TREATMENT APPARATUS AND CONTROL METHOD THEREFOR

CROSS-REFERENCE TO RELATED APPLICATIONS

The present specification is a U.S. National Stage of International Patent Application No. PCT/KR2015/008893 filed Aug. 25, 2015, which claims priority to and the benefit of Korean Patent Application No. 10-2015-0118981 filed in the Korean Intellectual Property Office on Aug. 24, 2015, the entire contents of which are incorporated herein by reference.

TECHNICAL FIELD

The present invention relates to an optical treatment apparatus and a method of controlling the same, and more particularly, to an optical treatment apparatus and a method of controlling the same that control treatment contents by sensing the state of a treatment region while the treatment is proceeding.

BACKGROUND ART

Recently, technology for changing a state of tissue in such a way that energy is transferred by light irradiation to the human body tissue has been widely applied. Particularly, a treatment apparatus using a laser is widely used for various lesions such as skin diseases, eye diseases, neurological diseases, joint diseases, gynecological diseases, etc. A treatment apparatus using a laser is widely used for various lesions such as skin diseases, eye diseases, neurological diseases, joint diseases, gynecological diseases, etc. Such a treatment apparatus is disclosed in various documents, including Korean patent laid-open publication No. 10-2014-0009846.

At this point, in order to confirm whether or not the treatment is proceeding properly and prevent damage from occurring in the target and its adjacent locations due to irradiation of excessive light it is necessary to continuously monitor the state of the treatment region. However, in the case an optical sensor such as a charged coupled device (CCD) or a complementary metal-oxide semiconductor (CMOS), ultrasound, or etc. is used as in the conventional art, it is impossible to monitor the internal state of the treatment region or there is a limitation in sensing a minute change in the tissue.

DISCLOSURE

Technical Problem

In order to solve the above-mentioned problems, the present invention has been made to provide an optical treatment apparatus and a method of controlling the same that can monitor in real time a state change in the inside of the tissue of the treatment region during treatment and perform treatment based on the monitoring.

Technical Solution

In order to achieve the object described above, the present invention provided an optical treatment apparatus, including: a treatment beam generation unit for generating a treatment beam; a beam delivery unit for forming a path through which the treatment beam generated from the treatment beam generation unit proceeds to a treatment region; a monitoring unit for irradiating the treatment region with a detection beam and sensing state information about the treatment region based on interference information by the detection beam reflected from the treatment region; and a control unit for controlling operation of the treatment beam generation unit based on the state information about the treatment region sensed in the monitoring unit.

Here, while the treatment beam is irradiated onto one treatment position, the monitoring unit irradiates the treatment position with the detection beam a plurality of times, thereby sensing state information about the treatment position. Also, the monitoring unit compares interference information by each detection beam with interference information by a detection beam irradiated previously, thereby determining a state change in the treatment region.

At this time, the monitoring unit is configured to selectively extracts information corresponding to a depth region of interest among the interference information by the detection beam, and to determines state information about the treatment region based on the information corresponding to the depth region of interest.

Here, based on the interference information by the detection beam, the monitoring unit senses a temperature change of the treatment region generated by absorption of the treatment beam into the treatment region. Specifically, the monitoring unit can sense temperature of the treatment position by comparing prestored reference data with the interference information.

Furthermore, the monitoring unit may be configured to include at least two algorithms for sensing the state of the treatment region, and to generate an error signal in the case the state information sensed from the respective algorithms has a difference of more than an allowable range.

Such an optical treatment apparatus may be configured to treat any lesion of the skin, the retina, or the trabecular meshwork tissue of the anterior segment.

Meanwhile, in order to achieve the object of the present invention described above, the present invention further provides a method of controlling an optical treatment apparatus, the method including the steps of: irradiating a treatment region with a treatment beam by driving a treatment beam generation unit; irradiating a treatment region, onto which the treatment beam is radiated, with a detection beam by driving a monitoring unit and sensing state information about the treatment region based on interference information about the detection beam reflected from the treatment region; and adjusting, by a control unit, operation of the treatment beam generation unit based on the sensed state information.

Here, the step of sensing the state information about the treatment region is configured to include selectively extracting information corresponding to a depth region of interest among the interference information by the detection beam; and comparing the extracted information about the depth region of interest with information about the depth region of interest by a detection beam irradiated previously.

Then, the step of comparing the information about the depth region of interest is performing a cross-correlation calculation of the extracted information about the depth region of interest and the information about the depth region of interest by the detection beam irradiated previously.

Further, the step of sensing the state information about the treatment region is configured to further include determining a temperature of the treatment region by referring to prestored reference data, thereby determining temperature information about the treatment region corresponding to the calculated value.

Advantageous Effects

According to the present invention, treatment is performed by detecting state information about the treatment region, so that optimized treatment is possible, and it is possible to prevent the adjacent region other than the treatment region from being damaged.

Further, the state information is sensed by using a speckle pattern of the detection beam, so that it is possible to proceed with the treatment by reflecting a minute state change. Also, information only about a specific region among the acquired information is extracted and then analyzed, so that the time to be consumed for analysis is minimized, thereby enabling near real-time monitoring.

MODE FOR INVENTION

Figure 1:
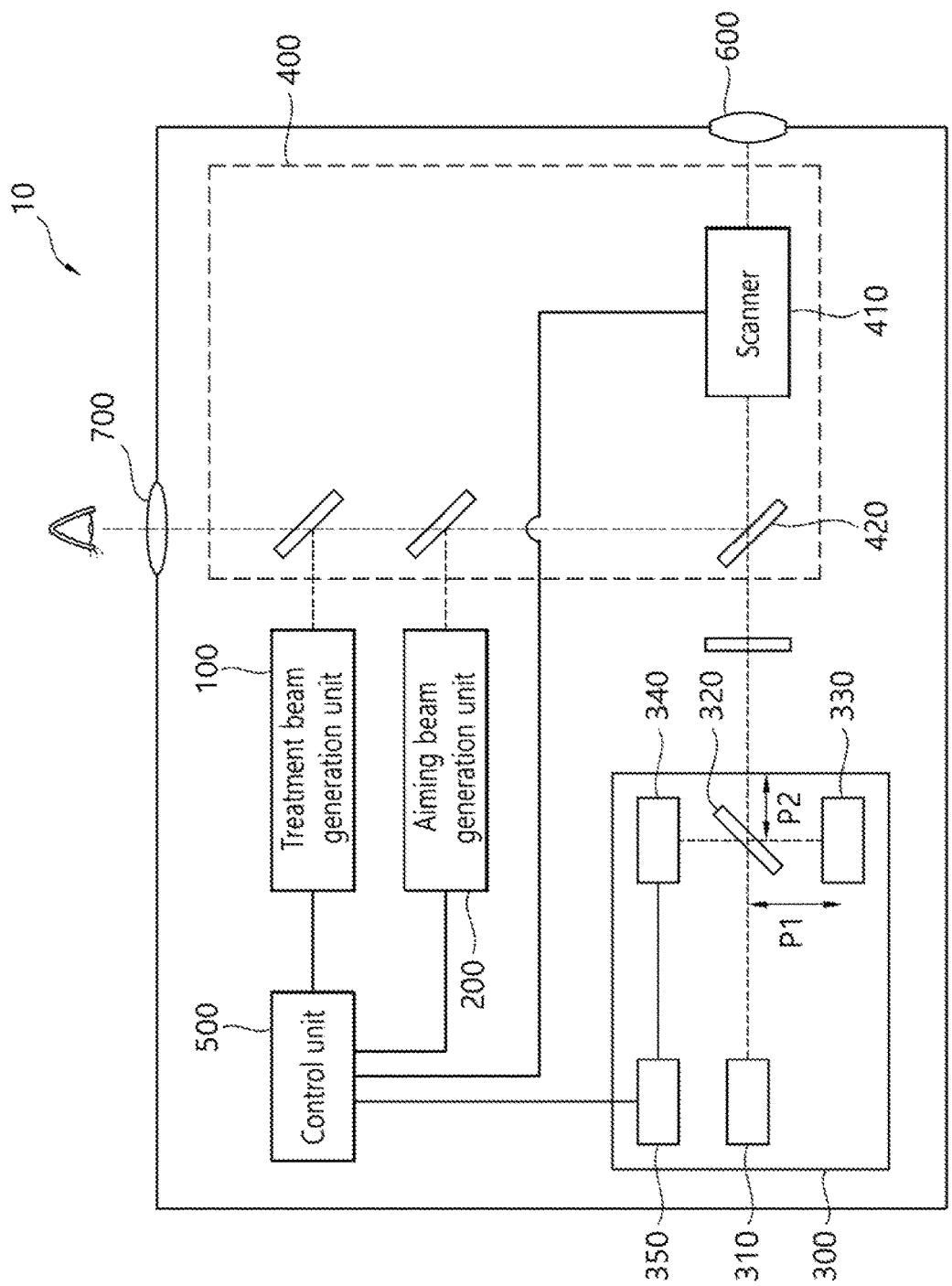
FIG. 1 is a schematic view schematically showing an optical treatment device according to an embodiment of the present invention.

Hereinafter, an optical treatment apparatus according to an embodiment of the present invention will be described in detail with reference to the drawings. In the following description, the positional relationship of each component is principally described based on the drawings. The structure of the invention in the drawings may be illustrated, for the convenience of description, as simplified or exaggerated if necessary. Therefore, the present invention is not limited thereto, and other than these, various devices may be, of course, added, changed, or omitted.

The optical treatment apparatus described below can be used for treating various lesions. For example, it may be applied to treat lesions generated in the retina tissue, may be applied to treatment for the anterior segment as a target tissue, and may be applied to treat lesions of the skin tissue. Therefore, it should be noted that the use of the present invention is not limited to the lesions described in the following examples, and it can be widely applied to various lesion treatments.

FIG. 1 is a schematic view schematically showing an optical treatment device according to an embodiment of the present invention. As shown in FIG. 1, an optical treatment apparatus 10 according to the present invention includes a treatment beam generation unit 100 for generating a treatment beam, an aiming beam generation unit 200 for generating an aiming beam, and a beam delivery unit 400 for forming a travel path of the treatment beam and the aiming beam. Furthermore, the apparatus further includes a monitoring unit 300 for sensing state information about a treatment region, and a control unit 500 for controlling the driving of the treatment beam generation unit based on the information sensed by the monitoring unit.

The treatment beam generation unit 100 may be configured to include a treatment beam-light source and various optical elements for processing characteristics of the light generated from the treatment beam-light source. The treatment beam is composed of a laser, and the treatment beam-light source may be configured to include a laser medium such as Nd: YAG, Ho: YAG or the like or a laser diode, capable of oscillating a laser. The treatment beam-light source is designed to irradiate a laser having a suitable wavelength in consideration of lesion contents or the characteristics of the target tissue to which energy is transferred. Also, various devices such as various electric circuits for exciting a laser, optical filters, shutters, etc. may be included in the treatment beam-light source.

On the one hand, the aiming beam generation unit 200 is configuration for generating an aiming beam to be irradiated onto the treatment region. The aiming beam is also a configuration for informing the operator of the position onto which the treatment beam is to be irradiated before the treatment beam is irradiated or while the treatment beam is being irradiated. The aiming beam has a wavelength of the visible light band, so the operator can confirm the treatment region by the aiming beam reflected from the treatment region.

The aiming beam generation unit 200 may irradiate an aiming beam in a single spot shape corresponding to the position onto which the treatment beam is irradiated. Alternatively, it is also possible to simultaneously irradiate a plurality of spots so that a pattern in which the treatment beam is successively irradiated can be displayed. In addition to this, the aiming beam may be irradiated in the form of a lattice or a boundary line to display a region to be irradiated with the treatment beam.

However, if it is possible for the operator to confirm the treatment region through a separate interface such as a monitor, the aiming beam generation unit may be implemented as being omitted.

On the other hand, the beam delivery unit 400 is composed of a plurality of optical elements and constitutes an optical path through which the treatment beam travels. Also, the aim beam, and a detection beam of the monitoring unit which will be described later, also travel along the beam delivery unit. In this case, the aiming beam and the detection beam may be configured to share at least part of the optical path of the treatment beam, or it is possible to configure to have their own separate optical path.

Specifically, as shown in FIG. 1, the beam delivery unit includes a plurality of beam combiners 420. By this, the treatment beam, the aiming beam, and the detection beam can respectively pass through the beam delivery unit and be irradiated onto the treatment region. Then, the aiming beam and the detection beam reflected from the treatment region may be directed toward the lens 700 where the operator's eye is located through the beam delivery unit 400 or may be incident on the monitoring unit 300 again.

The beam delivery unit 400 may include a scanner 410 for changing a position onto which the beam is irradiated. The scanner 410 is configured to include at least one reflecting mirror and a driving unit for rotating the reflecting mirror, so that the position onto which the beam is irradiated can be changed as the rotating position of the reflecting mirror from which the beam is reflected changes.

In addition, the beam delivery unit 400 may be configured to further include optical elements (not shown) such as a plurality of optical lenses for converging or diverging light, optical filters, etc.

At the end of the beam delivery unit 400, there may be provided an objective lens 600. The treatment beam, the aiming beam or the detection beam traveling proceeding through the beam delivery unit is converged while passing through the objective lens, and then irradiated onto the treatment region.

Figure 2:
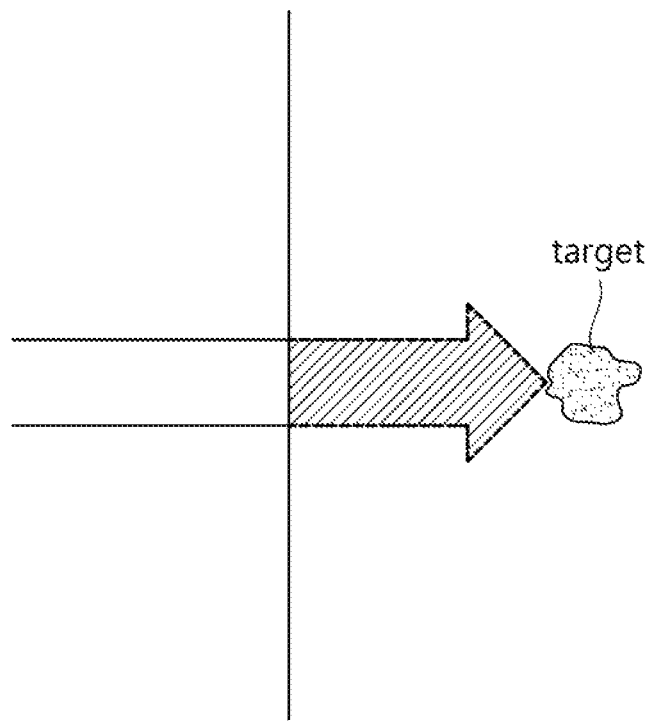
FIG. 2 is a view showing a state in which a treatment beam is irradiated onto a target position.

FIG. 2 is an enlarged cross-sectional view illustrating a patient's treatment region. A target tissue may be located on the surface of the tissue, but as shown in FIG. 2, depending on a lesion, may be an internal tissue disposed a predetermined depth inward from the surface of the tissue. The treatment beam irradiated from the optical treatment apparatus is absorbed into the target tissue of the treatment region. As the energy absorbed by irradiation of the treatment beam increases, the temperature of the target tissue rises, so that there occurs thermal denaturation in the target tissue. Here, the thermal denaturation refers to a change in characteristics of tissue caused by a rise in temperature, tissue necrosis or tissue regeneration. By such thermal denaturation, treatment of the target tissue can be achieved.

In this regard, if the treatment beam is excessively irradiated, there may occur thermal damage not only to the target tissue but also to the adjacent tissue. Accordingly, the optical treatment apparatus of the present embodiment includes the monitoring unit 300, and the monitoring unit 300 senses state information about the treatment region while the treatment is proceeding.

The monitoring unit 300 irradiates the treatment region with the detection beam. The detection beam reaching the treatment region is reflected by mediums of the treatment region, moves in the reverse direction of the travel path, and then is received again by the monitoring unit 300. Here, the detection beam is composed of light having a wavelength which is less absorbed by the tissue and has excellent transmittance so that the detection beam can reach the target tissue even when the target tissue is located within a predetermined depth from the surface of the treatment region.

The detection beam passing through the treatment region is scattered or reflected as it passes through tissues having different refractive indexes or passes through the interface of tissues. Thus, the reflected detection beam may be a combination of the light reflected at various depths of the treatment region. For example, in part of the reflected detection beam, there may exist light reflected from the surface of the treatment region, light reflected after proceeding to the first depth of the treatment region, and light reflected after proceeding to the second depth of the treatment region. Thus, the reflected detection beam may include state information about the tissue located at each depth from the surface of the treatment region to the target location.

Accordingly, the monitoring unit 300 can sense information about a state change in the treatment region by analyzing a change in interference information by the received detection beam. Here, the information about the state change in the treatment region includes at least one of information about the temperature change, the volume change, or the refractive index change of tissue, or whether or not cells are moved, which occurs in the treatment region while the treatment beam is being irradiated, and also refers to the aforementioned thermal denaturation of tissue. When the treatment beam is irradiated onto the treatment region, the temperature of the tissue rises, and by this, the volume of the tissue changes, the tissue characteristics change, or part of the tissue moves, thereby changing the travel characteristics of light passing through the tissue (for example, an optical path length, a speckle pattern, etc.). Therefore, while the treatment is proceeding, the interference information caused by the detection beam also changes, so that the monitoring unit can sense a state change in the treatment region based on the change in the interference information.

Specifically, the monitoring unit 300 according to the present embodiment may be configured using an Optical Coherent Tomography (OCT) apparatus. Such an OCT apparatus is a configuration for acquiring tomographic information about tissue using interference information of light. According to the driving method and the measuring method of the apparatus, there are types such as Time Domain OCT (TD OCT), Spectral Domain OCT (SD OCT), Swept Source OCT (SS OCT), etc. In present embodiment, SD OCT or SS OCT may be used. However, while conventional OCT acquires tomographic information by moving a coordinate horizontally (B-scan), the present embodiment is configured to acquire tomographic information about tissue at the same position by performing a Z-scan without a separate B-scan while monitoring for a specific treatment position is proceeding.

As shown in FIG. 1, the monitoring unit 300 is configured to include a light source 310, a beam splitter 320, a reference beam reflector 330, a detector 340, and a processor 350.

The light source 310 may be a light source generating a low coherent beam in the case of SD OCT, and a swept source light source capable of changing a wavelength of light may be used in the case of SS OCT.

The light emitted from the light source 310 is spilt into two beams, i.e., a detection beam and a reference beam. The reference beam travels along a first path P1 in the direction of the reference beam reflector, and then is reflected from the reference beam reflector 330. The detection beam travels along a second path P2, travels to the treatment region through the beam delivery unit 400, and then is reflected. Part of the reflected detection beam and part of the reflected reference beam are combined by the beam splitter 320 and are incident on the detector 340.

The combined detection beam and the reference beam may be interfered with each other, and the detector 340 may sense state information about the treatment region by using interference information about the received reference beam and the received detection beam. Here, the detector 340 may be configured to use an array detector in the case of SD OCT, and a photo diode in the case of SS OCT.

Specifically, when the detection beam and the reference beam are incident on the detector in a state that they are combined each other, it is possible to separate them into each wavelength band and acquire state information according to a depth of the treatment region by using a signal to which the Fourier transform-processing has performed. From the signal detected by the detector, various types of information about the treatment region can be acquired according to the treatment contents, and in the case of the present embodiment, information about a speckle pattern of the detection beam can be acquired.

Generally, when a laser light source with strong coherence is reflected from an irregular surface, the irregular surface causes random interference effects to occur. Regarding this phenomenon, in the initial stage, the term "granularity" had been used and was replaced by the term "speckle." The probability distribution function of a typical speckle pattern shows a tendency of a negative exponential function.

In fact, in the initial stage of laser researches, speckle was regarded as noise and treated as a cause of degradation in resolution, so that many efforts had been made to remove speckle. However, recently, as the statistical analysis of speckle has been made, practical applications thereof are attracting attention.

These days, speckle is defined as an OCT signal obtained from a backscattered laser with partial coherence from tissue. If an OCT image is obtained from a stationary object, a speckle pattern thereof will also exhibit stationary characteristic in terms of time. If there are moving particles due to movement of the tissue, a speckle pattern thereof will also change over time, and the degree of movement will be known by calculating the speckle variance between pixels, between lines and between frames. The speckle variance $SV_{ijk}$ obtained from an OCT Intensity $I_{ijk}$ is obtained by the following equation.

$$SV_{ijk} = \sigma_I^2 = \frac{1}{N} \sum_{ijk=1}^{N} \left( I_{ijk} - \frac{1}{N} \sum_{ijk=1}^{N} I_{ijk} \right)^2 = \frac{1}{N} \sum_{ijk=1}^{N} (I_{ijk} - I_{mean})^2$$

Here, N is the total number of pixels involved in the variance calculation, and i, j, and k represent indexes between pixels, between lines, and between frames of A/B/C scans. Referring to the statistical characteristics of $SV_{ijk}$ obtained by the above equation, it has been revealed by experiments that different characteristics are shown depending on types of tissue. When the tissue is solid, it shows the characteristic of Gaussian distribution, and when the tissue is fluid, it shows Rayleigh distribution characteristic. This means that the measurement accuracy of the $SV_{ijk}$ value obtained may vary depending on the sample tissues.

As such, a speckle pattern means an intensity pattern generated by mutual interference between beams constituting light. Such a speckle pattern may form a different pattern depending on the position of the optical path, and in each speckle pattern, scattering information generated when the beam passes through tissue, surface characteristics of the reflection surface, etc. are reflected. When a minute change in the optical path occurs, the interference pattern between the beams also changes whereby the speckle pattern at the corresponding position changes.

As described above, in the speckle pattern of the detection beam detected by the detector 340, state information about the treatment region is reflected. Therefore, it is possible to sense a minute state change in the treatment region, such as a rise in temperature, a change in tissue thickness, a change in refractive index, and a movement of tissue, by detecting a change in the speckle pattern during treatment.

Accordingly, the processor 350 determines a state change in the treatment region by analyzing a change in a signal (for example, speckle pattern) detected by the detector 340. When the state change in the treatment region is sensed, information about the state change can be provided to the control unit 500 so that the treatment contents can be changed to reflect the state change.

Figure 3:
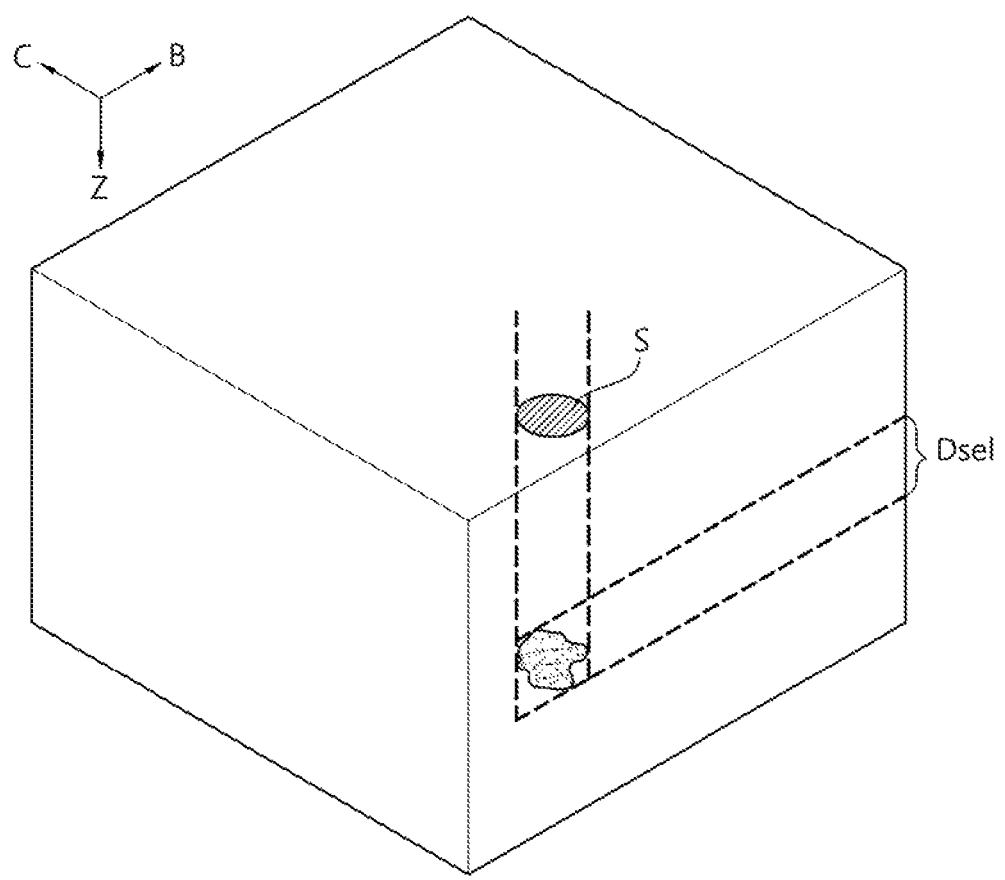
FIG. 3 is a view showing a tomographic structure irradiated with the treatment beam and a detection beam.

FIG. 3 is a view showing a tomographic structure of the treatment region irradiated with the treatment beam and the detection beam. As described above, the monitoring unit 300 irradiates a treatment region S with the detection beam while the treatment is proceeding, and senses a change in state information about the treatment region by using the reflected detection beam (see FIG. 3).

More specifically, the light source 310 irradiates the treatment region S with the detection beam a plurality of times while the treatment is proceeding. For example, the same treatment region may be irradiated with the treatment beam a plurality of times, and the detection beam may be irradiated simultaneously with the treatment beam or alternately with the treatment beam. Then, the detector 340 continuously detects a signal by the reflected detection beam. The signal obtained at the detector includes state information about the treatment region at that time. Accordingly, the monitoring unit 300 according to the present embodiment is capable of acquiring in real time state information about the treatment region by each treatment beam.

The processor 350 can sense whether or not the state change of the treatment region has been made in the manner of comparing signals detected by respective detection beams. For example, a signal detected by each detection beam (for example, a $n^{th}$ detection beam) and a signal detected by a detection beam irradiated previously (for example, a n-$1^{th}$ detection beam) are cross-correlated and based on the cross-correlation analyzed value, it is possible to determine whether or not the state change has been made. Alternatively, it is also possible to determine whether or not the state change has been made based on a value obtained by cross-correlation analysis of a signal detected by each detection beam and a reference value (for example, a signal by a first detection beam). In the present embodiment, a signal to be subjected to the cross-correlation calculation is a speckle pattern signal detected by the detector, but various types of signals other than the speckle pattern signal may be used.

Figure 4:
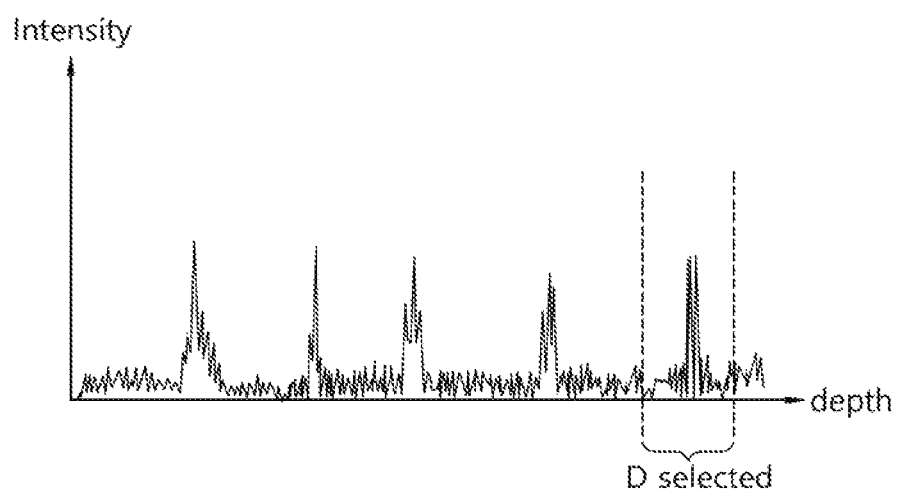
FIG. 4 is a graph showing an example of a signal detected by a detector.

FIG. 4 is a graph showing an example of a signal acquired by the processor unit. Here, the signal detected by the detector 340 includes information about every depth of the treatment region corresponding to the travel path of the detection beam. Therefore, in the present embodiment, only the information about a specific region of interest (hereinafter, referred to as a 'depth region of interest') Dsel is selectively extracted from signals detected by the detector, and then, based on the extracted information about the depth region of interest, it is possible to sense whether or not a state change has been made.

In the case of Swept Source OCT (SS OCT), the above description may be explained as follows. A sample of an interferometer and a beam returned from a reference mirror, both of the interferometer and the reference mirror being used in SS-OCT, will interfere with each other. This is expressed by the following equation.

$$I=|E_r+E_s|^2=|E_r^*E_s^*||E_r+E_s|=I+I+2\sqrt{I_rI_s}\cos(2kz)$$

Here, z represents a path difference between the reference mirror and the sample. The wave number k and the wavelength λ of the laser beam are expressed as follows.

$$k = \frac{2\pi}{\lambda}$$

The swept source wavelength conversion laser used in SS-OCT is a laser of which wave number changes linearly with time. Therefore, the changing laser wave number is expressed as follows.

$$k = k_0 + \alpha t$$

In the above equation, $k_0$ is the initial wave number and $\alpha$ is a constant. Here, assuming that the signal detected by the detector is simplified to monochromatic light, the time-averaged photocurrent (I) and the interference term to be finally obtained are the same as the above-respectively mentioned equations. Instead of the wavelength used in the above equation, the wave number can be substituted and expressed as follows.

$$\text{real}(E_S E_R) = A_R A_S \cos(2k\Delta L)$$

In the above equation, z is the depth in the sample with the path difference $\Delta L$ between the reference mirror and the corresponding point of the sample.

$$\text{real}(E_S E_R) = A_R A_S \cos(2kz)$$

If the laser wave number is substituted in the above equation, it can be expressed as follows.

$$\text{real}(E_S E_R) = A_R A_S \cos(2(k_0 + \alpha t)z) = A_R A_S \cos(2k_0 z + 2\alpha z t) = A_R A_S \cos(\Phi_0 + \Phi(t))$$

In this equation, $\Phi_0 = 2k_0 z$, $\Phi(t) = 2\alpha z t = \omega t$, and $\omega = 2\alpha z$ can be summarized as follows.

$$\text{real}(E_S E_R) = A_R A_S \cos(\omega t + \Phi_0)$$

Here, when compared with the general form of the cosine function, $\omega = 2\alpha z$ and $\Phi_0$ indicate frequency and phase angle, respectively, and can be expressed by the following equation.

$$2\pi f = 2\alpha z$$
$$f = \frac{\alpha}{\pi} z$$

Consequently, the above equation means that the specific frequency of the signal incident on the detector corresponds one-to-one with a specific depth in the sample. The frequency component of the spectral density function obtained by Fourier transforming the interference signal represents depth information about the sample, and the magnitude of each frequency component represents the relative intensity of light at each depth.

Finally, when the signal obtained by the detector is Fourier-transformed, the component according to the frequency of the signal can be known, and the amplitude of the specific frequency means the information of backscattered light at a specific depth. If the interference signal, which is generated when the light source is sequentially converted from a short wavelength to a long wavelength or from a long wavelength to a short wavelength without moving the reference mirror, is received by the detector, and then the Fourier transform is performed to the signal, it has the same effect as receiving a signal at the corresponding sample depth by moving the reference mirror.

Assuming that a Gaussian-type light source with a wide wavelength is used, the wavelength conversion laser has a filter with a narrower width than that of the wavelength in such a way that while the filter moves from a short wavelength to a long wavelength or a short wavelength to a long wavelength in a spectrum of the light source, light having a line width of a wavelength corresponding to the position of the filter is generated. In SS-OCT, as the line width of this filter is narrower, the imaging depth is deeper.

On the basis of time, the narrow-width light is sequentially irradiated onto the sample and the backscattered light is input to the detector as an interference signal. Since the narrow width light generates interference when it enters the detector, the interference occurs, resulting in highly coherent light rather than low coherent light. Therefore, the coherence length is long, and the detector senses backscattering information from every depth where the light of the sample reaches and is backscattered, so that the light can be returned. As the coherence length is longer, the scattered backscattered light at the deeper part of the sample can cause interfere and the interfering signal can be received and then imaged by the detector. That is, as the line width of the filter is narrower, imaging can be performed to a deeper part of the sample.

Specifically, when a signal is detected by any one of the detection beams, information only about the depth region of interest Dsel is extracted. Then, the processor 350 may determine whether or not a state change has been made by cross-correlating information about the depth region of interest by a current corresponding detection beam (for example, a $n^{th}$ detection beam) and information about the depth region of interest by a detection beam (for example, a $n-1^{th}$ detection beam) (Here, while the detection beam is continuously irradiated, the detection beam is irradiated on the same position without performing a B-scan).

In this case, a calculation amount to be processed is significantly reduced as compared with the case where calculation processing is performed using the entire detected signal, so that fast calculation is possible. Therefore, it is possible to monitor close to real time by minimizing the time required to analyze state information.

Further, in performing a calculation for sensing a change between a previous signal and a current signal, when only the signals of the depth region of interest where a state change exists most active are selected and compared each other, the rate of change appears significantly large. Therefore, it is possible to accurately determine whether or not the state change in the treatment region has been made.

Here, the depth region of interest Dsel may be a tissue to be a target during treatment, a tissue in which a state change occurs first, or a depth region in which a tissue having a large amount of the state change is located. For example, when treatment for RPE cells as a target tissue is proceeding, the depth at which the RPE cell layer is located in the retina tissue can be set as a depth region of interest. Alternatively, in the case of treating the cornea, it is possible to set a specific depth region in the stroma as a depth region of interest, and in the case of treating a skin lesion, it is also possible to set a depth of a specific tissue of the endothelium as a depth region of interest. In addition to this, the depth region of interest can be set differently depending on a treatment lesion.

This depth region of interest Dsel may use a predetermined value, in the present embodiment, however, the user can configure the depth range Dsel through an interface (not shown) in consideration of the treatment lesion and the characteristics of the patient. Since the shape and thickness of the tissue in the treatment region differ depending on the patient, after securing a tomographic image of the treatment region first, and then in consideration of this, it is possible to set a depth region of interest.

In this way, the processor 350 cross-correlates the extracted signals of the depth region of interest Dsel to determine a state change in the treatment region, and such a determination method can be configured in various ways.

For example, in the case the amount of change of the extracted signal is less than a predetermined value (first set value) as compared with the previous signal, it is determined that there is no state change in the treatment region, and in the case the amount of change is equal to or greater than a predetermined value, it is determined that there is a state change in the treatment region.

As another example, a temperature of the treatment region can be determined by comparing the signal value of the extracted signal (or the amount of change of the signal) with prestored reference data. Depending on the characteristics of the tissue, the signal value detected through the monitoring unit may not be linearly proportional to the amount of energy being delivered. For example, the signal value changes abruptly at a temperature where the tissue is denatured or necrotized. Therefore, when such denaturation or necrosis is not the goal of treatment or the completion of treatment, it may be difficult to determine whether or not treatment has been completed by the signal value. In addition, even if the denaturation or necrosis of the tissue is the target of treatment or the completion of the treatment, the change of the signal value is relatively minute before reaching the corresponding point, so that it is difficult to grasp information such as how close to the completion of the treatment is. Therefore, the optical treatment apparatus of the present embodiment can include a signal value (or an amount of change of the signal) detected by the detection beam and reference data for temperature information corresponding thereto. Also, the processor can compare the signal detected during treatment with the reference data to determine temperature information about the depth region of interest in real time. In this case, even before the denaturation or necrosis of the tissue progresses, it is possible to configure various contents of treatment while continuously sensing the temperature of the target tissue.

In addition to this, it is also possible to apply an ocular temperature measurement method using OCT, which can be broadly classified into two categories, i.e., one for phase-based methods and the other for intensity/speckle based methods The phase-based methods are divided into Doppler optical coherence tomography (D OCT), optical microangiography (OMAG) and phasvariance optical coherence tomography (PV-OCT), etc., and the intensity/speckle-based methods are divided into a Split-Spectrum Amplitude Decoration angiography (SSADA) algorithm, speckle variance optical coherence tomography (SV-OCT), etc.

In the case PV-OCT and SV-OCT is compared, they are quite similar to each other in terms of mechanism in that PV-OCT is for obtaining phase variance of OCT A/B/C scans obtained continuously at the same position of the sample and SV-OCT is for obtaining intensity/speckle variance. Also, compared to the other methods, PV-OCT and SV-OCT have independent characteristics in direction (in other words, direction cannot be measured). There is also a difference between PV-OCT and SV-OCT in that PV-OCT has a disadvantage in that background Doppler phase shifts caused by bulk motion in the axial direction has to be removed very precisely, and in that resolution is influenced by phase noise and tissue motion. In contrast, SV-OCT has an advantage of very simple processing, which requires only obtaining variance on A/B/C scans.

As such, the monitoring unit 300 according to the present embodiment can sense state information about the target tissue during treatment by selectively extracting signal information corresponding to the depth region of interest Dsel, i.e., the depth at which the target tissue is located. Particularly, it is possible to monitor not only information about a point when the treatment of the target tissue is completed during treatment, but also information about a minute state change during temperature rise in the process of treatment. Therefore, according to the present embodiment, it is possible to prevent thermal damage to the adjacent tissue due to excessive irradiation of the treatment beam, and it is possible to carry out optimal treatment by accurately transferring the desired amount of energy.

In the above description, the monitoring unit has been described focusing on the algorithm for sensing the state of the treatment region by using the interference information by the detection beam. However, in addition to this, the monitoring unit may be configured to include a plurality of algorithms for sensing the state of the treatment region. For example, it may be configured to further include an algorithm for sensing a change in a sound wave signal caused by denaturation of treatment tissue using a sound wave sensor, and to further include an algorithm for sensing an image change in the treatment region by using an image photographing apparatus.

In this case, the monitoring unit may select any one of a plurality of algorithms to sense the state of the treatment region in consideration of the contents of treatment or the target tissue. Alternatively, while simultaneously sensing the state of the treatment by using a plurality of algorithms, it is also possible to grasp a treatment state by comparing the values measured through the respective algorithms. In the case a value measured by each algorithm is deviates an allowable error, it is possible to be controlled to determine that an error has occurred in one of the algorithms, and then to transfer the error to the user.

Meanwhile, the control unit 500 a configuration to control operation of various components such as the treatment beam generation unit 100, the aiming beam generation unit 200, and the beam delivery unit 400. Here, state information about the treatment region sensed by the monitoring unit 300 is transferred to the control unit 500, and the control unit 500 can control various components based on the state information about the treatment region.

Among other things, the control unit 500 can control the operation of the treatment beam generation unit 100 according to the state information about the treatment region. For example, the parameters of the treatment beam such as the output of the treatment beam, the pulse time of the treatment beam, the time between pulses constituting the treatment beam, or the converging degree of the treatment beam can be controlled in various ways.

As such, the optical treatment apparatus 10 according to the present embodiment can monitor the progress of the treatment in the monitoring unit and in consideration of this, optimal treatment can be performed by controlling the contents of treatment in the control unit. The optical treatment apparatus like this may be configured to be used for treating various lesions. Hereinafter, examples of lesions to which the optical treatment apparatus can be applied will be described.

Retinal Lesion Treatment

Figure 5:
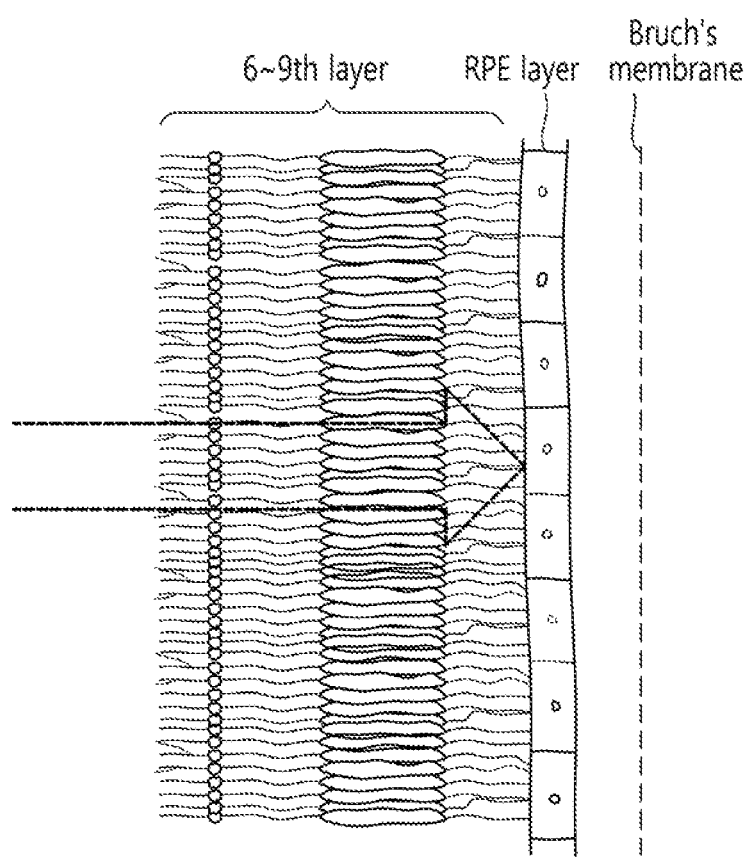
FIG. 5 is a view showing a tomographic structure irradiated with the treatment beam and the detection beam.

The optical treatment apparatus described above can be used for treating various lesions occurring in the fundus region, such as macular degeneration. FIG. 5 is a view showing retinal tissue of a patient corresponding to a treatment region.

As shown in FIG. 5, the retina tissue is generally formed with 10 layers of an internal limiting layer, a nerve fiber layer, a ganglion cell layer, an inner plexiform layer, an inner nuclear layer, an outer plexiform layer, an outer nuclear layer, an external limiting layer, a photo receptor layer, and a retinal pigment epithelial layer (RPE layer).

Among these, the RPE cell layer forms a boundary layer in the rear direction among the above ten layers, and is formed in a tight junction structure. Bruch's membrane is located on the underside of the RPE layer. This RPE layer supply nutrients and oxygen from blood vessels located under Bruch's membrane to photoreceptors and discharge waste generated from the photoreceptors through Bruch's membrane.

Here, when some RPE cells forming the RPE layer fail to perform their normal functions, photoreceptors corresponding to these RPE cells are normally not nourished or oxygenated whereby the photoreceptors are necrotized. Accordingly, the optical treatment apparatus according to the present embodiment RPE cells that do not perform their normal functions with treatment beam to selectively necrotize the RPE cells, thereby inducing regeneration of new RPE cells.

In order to proceed with this treatment, the optical treatment apparatus is provided with a contact lens (not shown) at a position adjacent to the objective lens 600, and the treatment is carried out with the patient's eye placed on the contact lens.

Then, the treatment beam generation unit 100 irradiates treatment beam having a wavelength in a visible light or near-infrared light region. Light with a corresponding wavelength passes through the cell layers (the first cell layer to the ninth cell layer) located in the front of the retina in a state almost not being absorbed, and then is absorbed into melanosomes existing in the RPE cells of the RPE cell layer. Therefore, as the amount of energy absorbed by the treatment beam increases, the amount of energy absorbed into the melanosomes increases, the temperature of the melanosomes rises, so that thermal damage to the RPE cells occurs. It is understood that microbubbles are generated on the surface of the melanosomes as the temperature rises and the RPE cells are selectively necrotized as the microbubbles gradually grow. Thereafter, treatment is made in such a way that new RPE cells are regenerated at the location of the RPE cells where thermal damage has occurred.

Here, when the treatment beam is excessively irradiated, thermal damage may occur not only to the RPE cells irradiated with the treatment beam but also to the adjacent RPE cells and photoreceptors. Accordingly, the monitoring unit 300 of the optical treatment apparatus senses state information about the treatment region while the treatment is proceeding.

Figure 6:
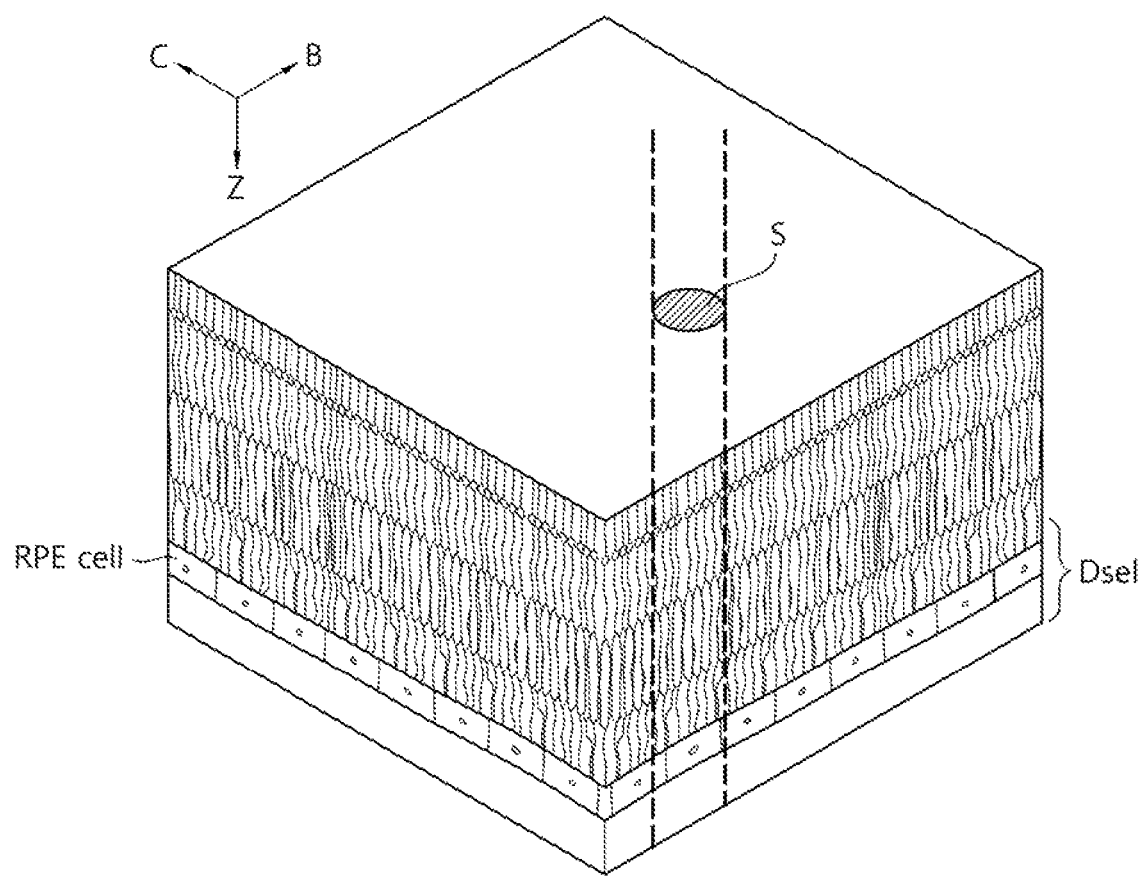
FIG. 6 is a graph showing an example of a signal detected by the detector.

The monitoring unit 300 uses an interference signal by the detection beam as described above. The signal acquired thereby may include all of state information about the photo receptor layer, the RPE cell layer, and the Bruch's membrane from the retina surface (See FIG. 6). Here, most of the treatment beam is absorbed into the RPE cell layer, and the state thereof changes as the temperature of the RPE cell layer rises. Thus, in present embodiment, the depth region of interest can be set to a depth including the RPE cell layer. For example, it is also possible to set a region from a 50% point to a 100% point of the thickness in the outward direction (downward direction with reference to FIG. 6) from the retina surface as the depth region of interest, and more specifically, it is also possible to set a region from a 70% point to a 100% point of the thickness as the depth region of interest.

As such, the monitoring unit selectively extracts only information about the depth region of interest (Dsel) including the RPE cell layer. Then, by comparing the signal extracted in the way as described above with the signal of the depth region of interest by the previous detection beam or with the reference value, it is possible to sense whether or not a state change in the treatment region has been made. The control unit may control treatment contents based on the state information about the treatment region sensed by the monitoring unit.

Hereinafter, a method of driving the optical treatment apparatus for treating the retina will be described in more detail.

Figure 7:
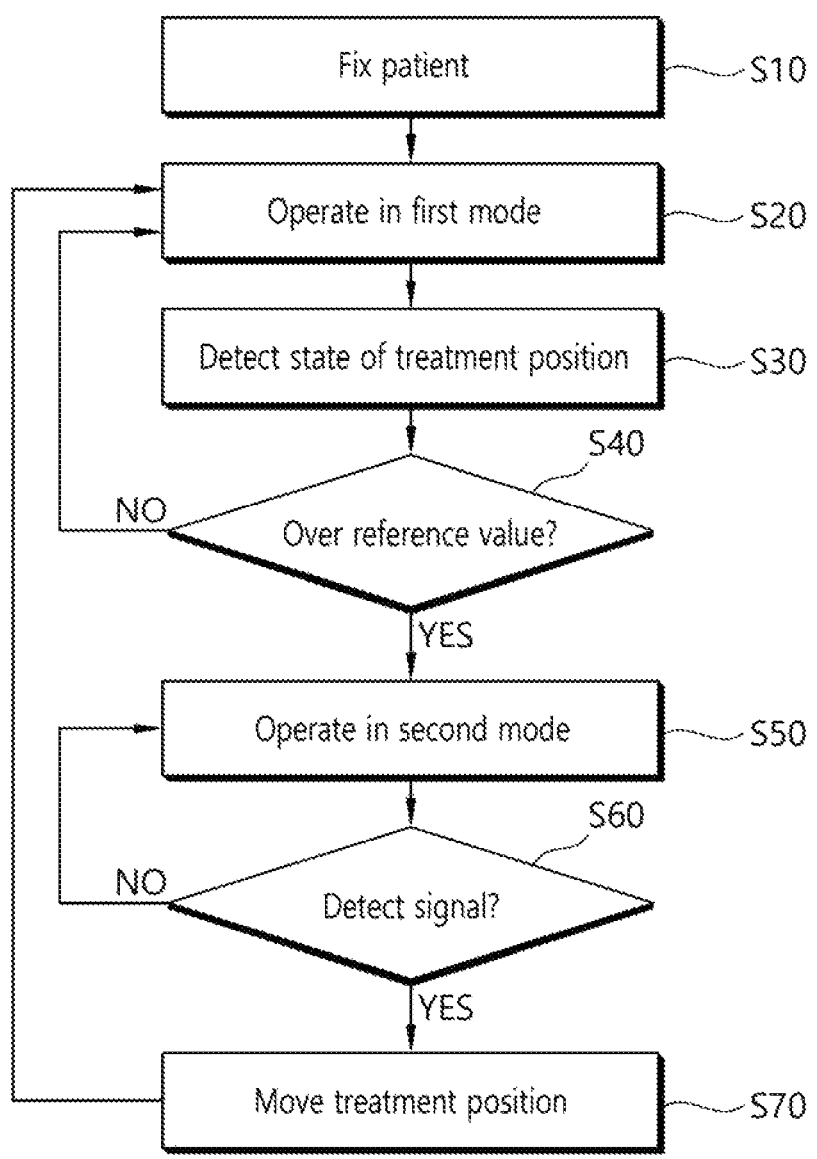
FIG. 7 is a flowchart showing a method of driving the optical treatment apparatus.

FIG. 7 is a flowchart showing a method of driving the optical treatment apparatus for retinal treatment. When a treatment region is determined according to the result of examination of a lesion of the patient, the eye of the patient is fixed to a contact lens unit 600 (S10).

A control unit 500 drives a treatment beam generation unit 100 to irradiate the fundus of the patient with treatment beam in a first mode M1 (S20). In the first mode, a treatment beam is irradiated a plurality of times, and the energy provided to a unit area of the treatment region per unit time is irradiated in a pattern increasing sequentially from low magnitude. By this, it is possible to prevent damage to the adjacent tissue due to transference of excessive energy to the treatment region.

While the above-described steps are proceeding, the monitoring unit 300 irradiates the position, which is being irradiated with the treatment beam, with a detection beam a plurality of times, receives a reflected detection beam, and continuously senses the state of the treatment region (S30). At this time, each detection beam may be simultaneously irradiated with the treatment beam, or the detection beam and the treatment beam may be alternately irradiated.

Figure 8:
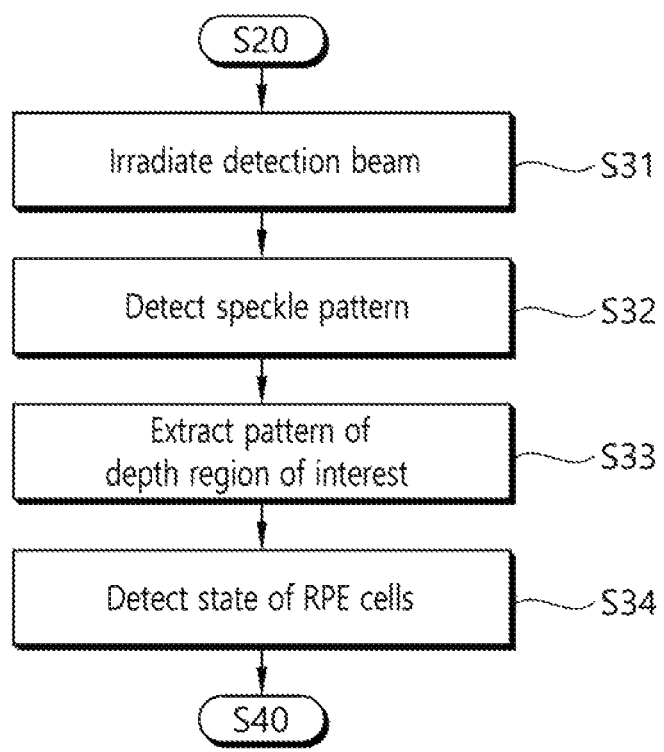
FIG. 8 is a flowchart specifically showing steps of sensing the state of a treatment region in FIG. 7.

FIG. 8 is a flowchart specifically showing steps of sensing the state of the treatment region in FIG. 7. Hereinafter, these steps will be described in more detail with reference to FIG. 8.

First, a light source of the monitoring unit 300 irradiates the treatment region, which is being irradiated with the treatment beam, with a detection beam (S31). The irradiated detection beam is scattered or reflected after traveling to the inside of the retina corresponding to the treatment region.

Then, the detector 340 detects a speckle pattern of the detection beam from interference information about the scattered or reflected detection beam and the reference beam (S32). Here, the speckle pattern of the detection beam may include information according to each depth of retinal cross-sections through which the detection beam has passed.

In the detected speckle pattern, a speckle pattern is extracted for a depth region of interest, that is, a partial region including a RPE cell layer (S33). The RPE cell layer is a region where a state change occurs most sensitive to the treatment beam. Therefore, the detector 340 or a processor 350 excludes information about unnecessary depth regions in the speckle pattern of the detected light, and extracts information about of the speckle pattern of the RPE cell layer of interest.

The processor 350 determines the state of the treatment region, specifically, the state of the RPE cell layer in the treatment region based on the extracted change information about the speckle pattern of the RPE cell layer (S34). At this time, the processor 350 senses the state of the treatment region in such a way that the amount of change is detected by cross-correlating information about a speckle pattern of the RPE cell layer by the current detection beam (for example, a $n^{th}$ detection beam) and information about a speckle pattern of the RPE cell layer by the previous detection beam (for example, a $n-1^{th}$ detection beam). Alternatively, it is possible to sense the state of the treatment region in such a way that the amount of change is detected by cross-correlating information about a speckle pattern of the RPE cell layer by the current detection beam (for example, a $n^{th}$ detection beam) and information about a speckle pattern of the RPE cell layer by the initial detection beam (for example, a first detection beam).

FIG. 8 shows steps of one of a plurality of detection beams irradiated in the monitoring process. However, in these steps, while the plurality of detection beams are irradiated, the above-described steps S31 to S34 are performed for every detection beam repeatedly, so that state information about the RPE cell layer in the treatment region can be continuously sensed during treatment.

Referring again to FIG. 7, when the state information about the treatment region sensed through the steps as described above is sensed, it is determined whether or not the state information has changed to a predetermined reference value or more(S40). At the present step, it is determined whether or not the amount of change of the speckle pattern in the above-described step is equal to or greater than a predetermined reference value. Based on this, the control unit can control treatment contents.

Meanwhile, the present invention is also capable of sensing a state pf the RPE cells in a way different from that described above. In the above, the monitoring unit is configured to sense the state change in the RPE cells using the amount of change of the speckle pattern by each detection light. In contrast, as another example, it is possible to sense the state of the RPE cells with a method of sensing a temperature value of the treatment region by using the speckle pattern generated by each detection beam (S34).

Figure 9:
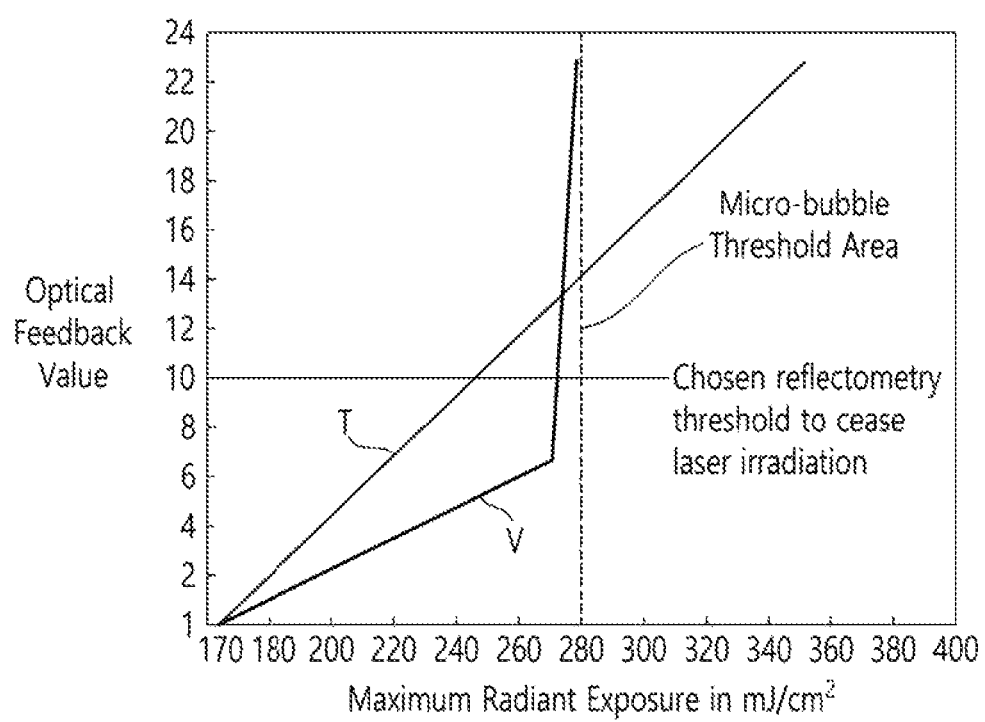
FIG. 9 is a graph showing values of interference signals and temperature changes by the detection beam as energy transferred by the treatment beam increases.

FIG. 9 is a graph showing values of interference signals and temperature changes by the detection beam as energy transferred by the treatment beam increases. As shown in FIG. 9, while the temperature rises linearly as the energy transferred increases (T), the interference signals by the detection beam change relatively finely, and at the time the RPE cells are necrotized, it shows a rapid changing aspect (V). Accordingly, in order to accurately determine the state of the treatment region from the time before the RPE cells is necrotized, it is possible to configure the temperature of the treatment region to be sensed by using separate reference data.

Figure 10A:
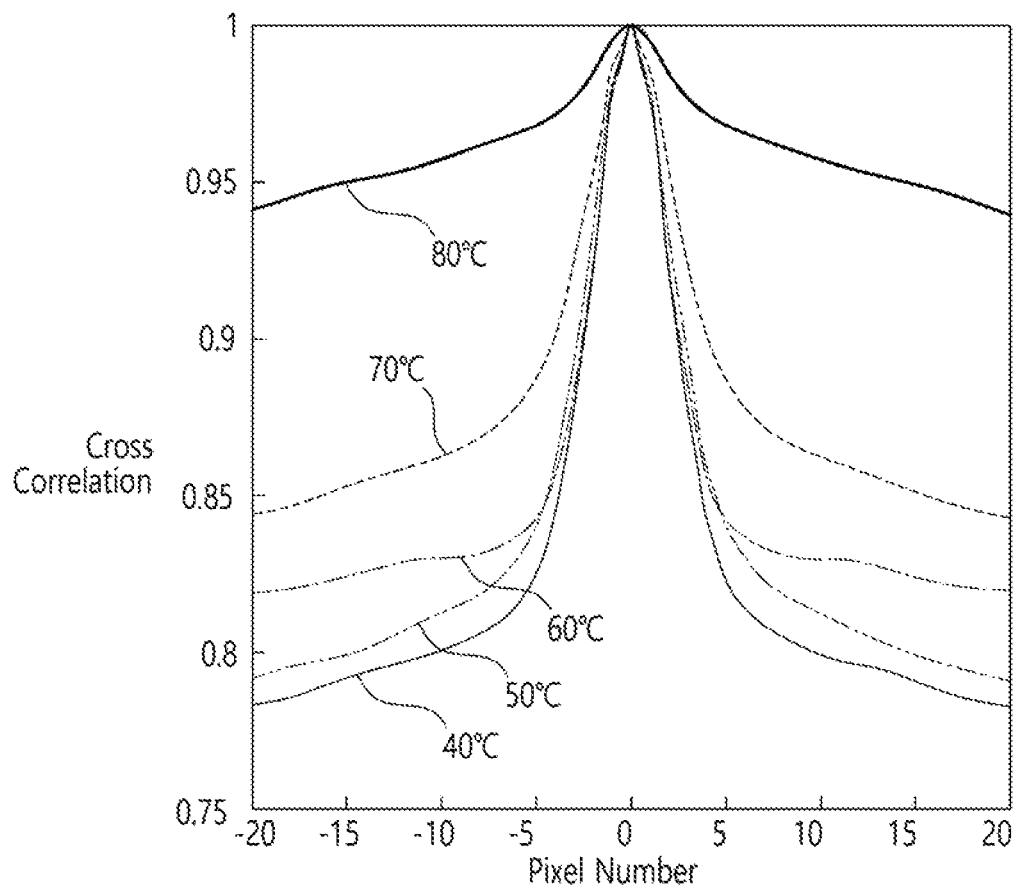
FIGS. 10a and 10b are graphs showing a relationship between the temperatures and the interference signals by the detection beam in FIG. 9, FIGS. 11a and 11b are graphs showing examples of a first mode operation and a second mode operation in FIG. 7, FIGS. 12a to 12d are graphs showing examples of the operation of the first mode of FIG. 7 according to another embodiment.
Figure 10B:
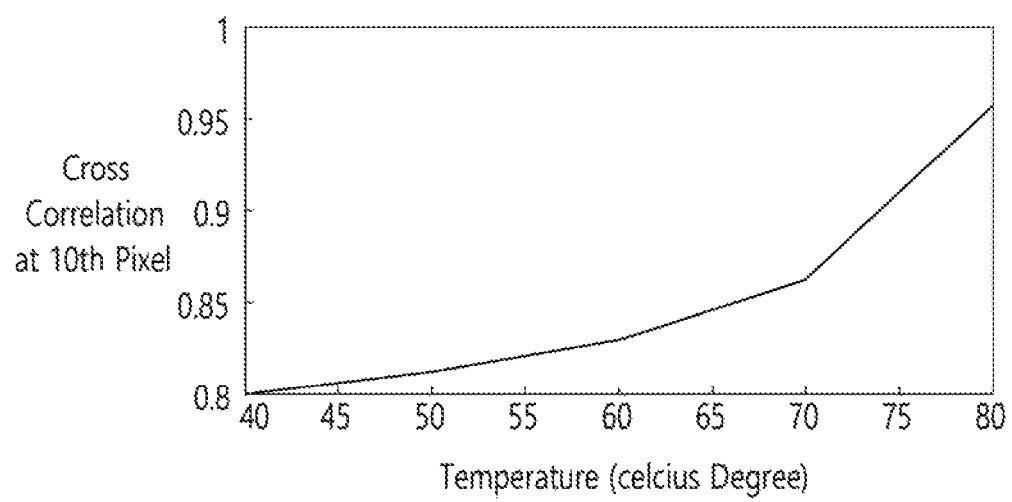

FIGS. 10a and 10b are graphs showing an example of reference data. In FIG. 10a, the distribution of the cross-correlation values of the speckle signals due to the interference light is shown, which shows a different distribution depending on the temperature. In the case of FIG. 10a, there is no temperature dependency for the values measured at pixel number 0, but for the values measured at pixel number 10 there is clearly a difference in value according to temperature. Therefore, as shown in FIG. 10b, it is possible to construct reference data indicating a correlation between the pixel number 10 and the temperature.

In this way, reference data between the detected value and the temperature can be variously configured by using a value having a definite difference according to the temperature among the values calculated by the signal sensed by the detection beam. Such reference data may be previously provided data. Alternatively, it may be possible to construct reference data by using measured values while irradiating a test region of the patient with a test beam before proceeding with the treatment.

In this way, when a speckle pattern corresponding to the RPE cell layer is extracted from the speckle pattern by the detection beam, in the manner of determining a temperature of the RPE cell layer by comparing a value obtained therefrom with a reference value, the monitoring unit can sense the state of the RPE cells (S34). Then, it determines whether or not the temperature of the RPE cells exceeds a predetermined reference value (for example, reference temperature) (S40), and based on this, the control unit can control treatment contents.

On the one hand, if it is determined by step S40 that the state information about the treatment region is equal to or less than the reference value, the control unit 500 can control the treatment to continue in the first mode M1 which is currently in progress. On the other hand, if it is determined that the state information about the treatment region exceeds the reference value, the control unit 500 can control the treatment beam generation unit to switch to a second mode M2 and operate in the second mode M2 (S50).

Figure 11A:
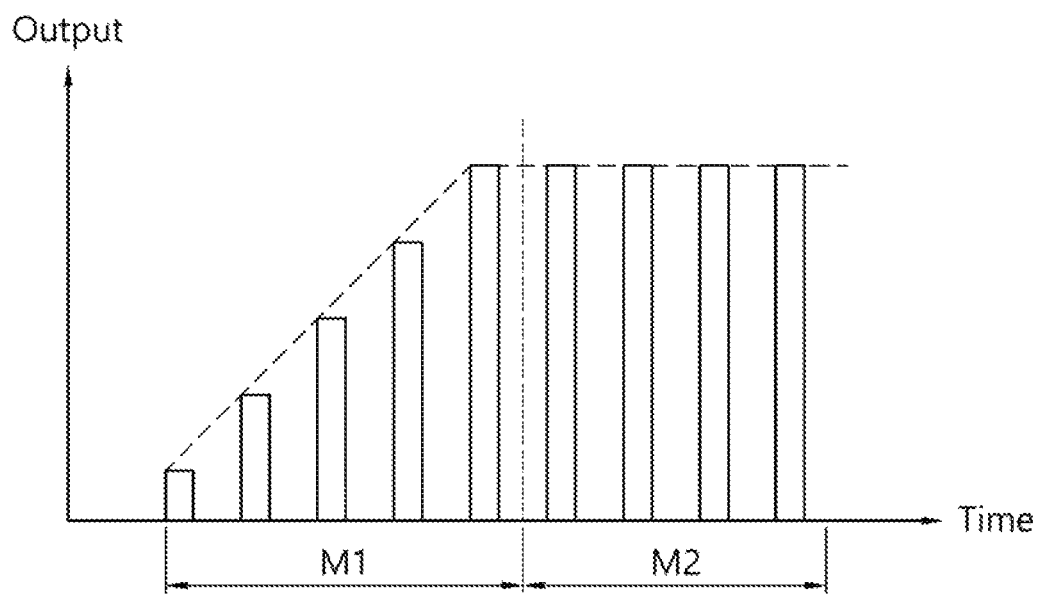
Figure 11B:
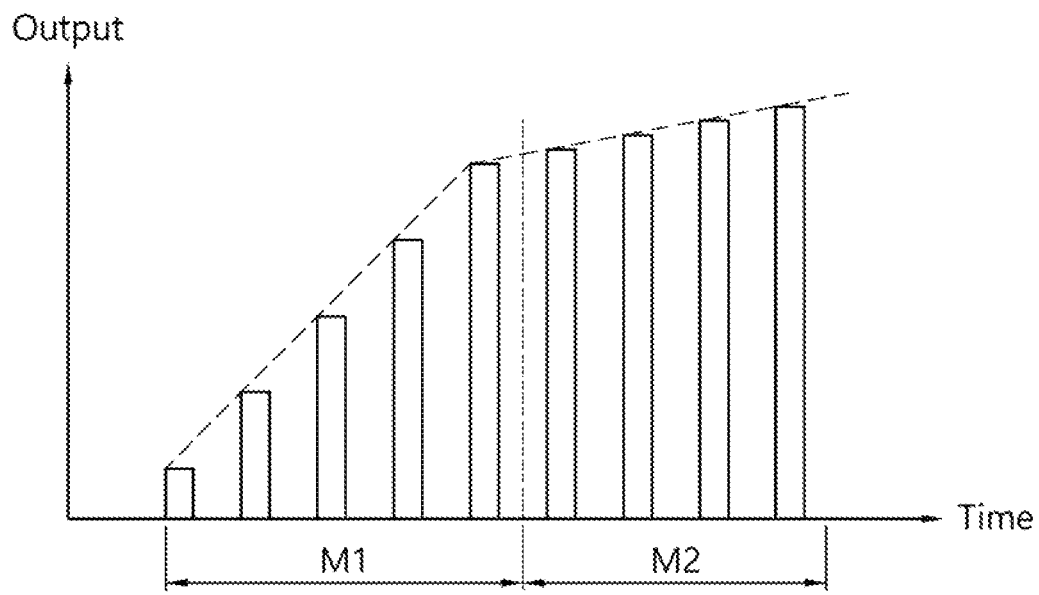

FIGS. 11a and 11b are graphs showing examples of a first mode operation and a second mode operation in FIG. 7. As described above, in the first mode M1, the treatment beam generation unit 100 generates the treatment beam so that the energy delivered to the unit area of the treatment region per unit time sequentially increases. In contrast, in the second mode M2, it is determined that the temperature of the RPE cells has increased to a temperature close to the predetermined temperature, so that the energy transferred to the unit area of the treatment region per unit time is not increased any more, and the treatment beam is generated to maintain the current state (FIG. 11a). Alternatively, it is also possible to generate the treatment beam to reduce an increase width of energy transferred to the unit area as compared with the first mode (FIG. 11b).

As such, the monitoring unit 300 monitors the state information about the treatment region based on the continuously detected signals while the treatment beam is being irradiated in the second mode M2. Then, it continuously determines whether or not a signal indicating whether or not the RPE cells has reached a predetermined temperature (for example, a signal corresponding to necrosis of the RPE cells) is sensed.

Through the above process, the operation of the second mode M2 can be continued until a treatment completion signal is sensed. When the treatment completion signal is sensed, irradiation of the treatment beam to the corresponding treatment region is terminated, and it is possible to change the irradiation position of the treatment beam to another treatment region to proceed with the treatment.

In the case of performing the driving method of the optical treatment apparatus described above, in controlling the first mode M1 for sequentially increasing the energy transferred to the unit area of the treatment region per unit time, the output of the treatment beam pulse in FIG. 11 is controlled in the manner of increasing sequentially. However, this is a mere example and it is also possible to implement the first mode by controlling other variables other than the output of the treatment beam.

Figure 12A:
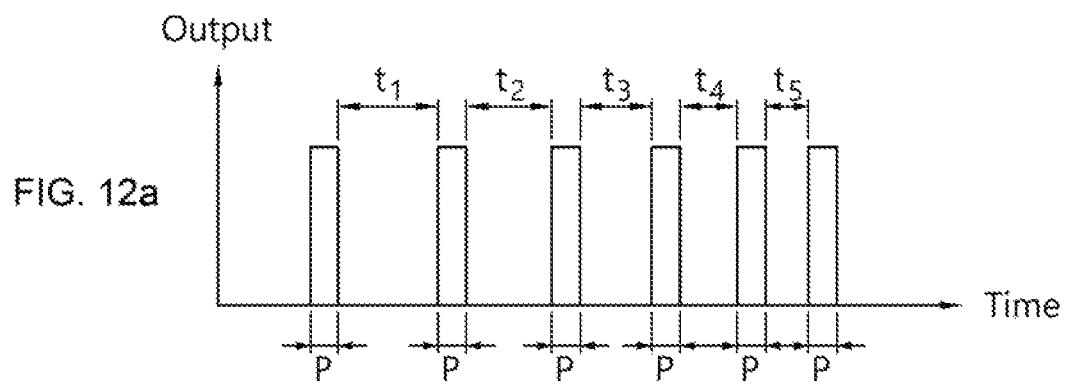
Figure 12B:
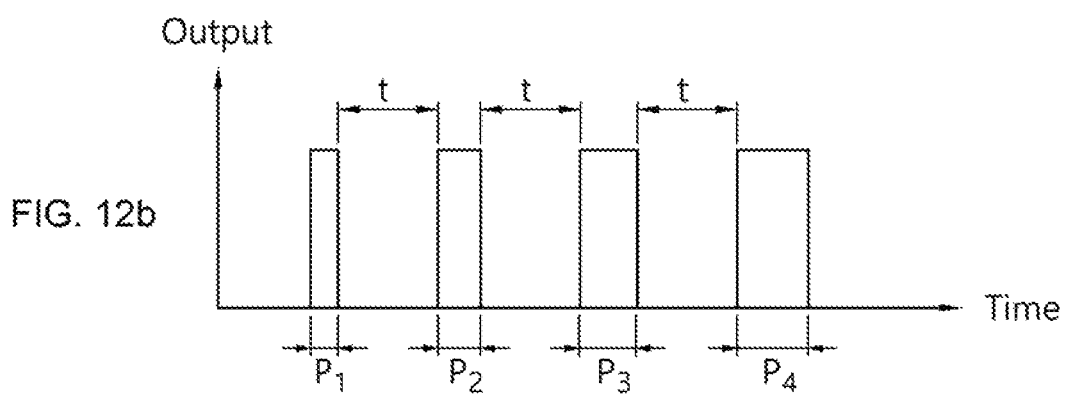
Figure 12C:
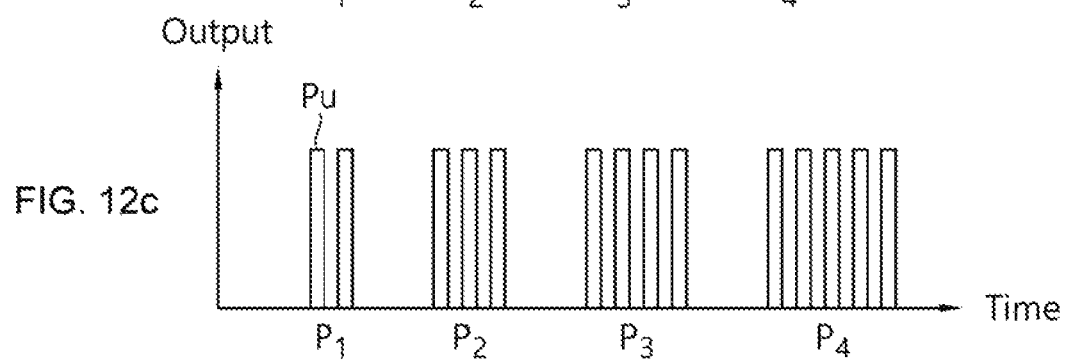
Figure 12D:
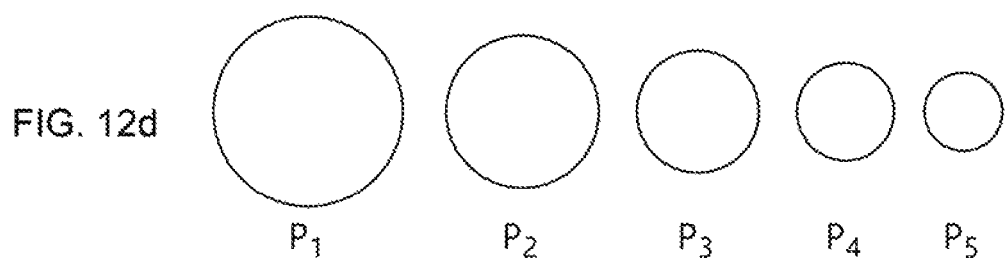

FIGS. 12a to 12d are graphs showing examples of the operation of the first mode of FIG. 7. For example, as shown in FIGS. 12a, the treatment beam generation unit generates pulses of the same output having the same pulse duration, and gradually reduces the off time between the pulses, so that the magnitude of the energy transferred per unit time can be sequentially increased. Alternatively, as shown in FIG. 12b, pulses of the same output are generated, and the pulse duration of each pulse is gradually increased, so that the amount of energy transferred per unit area can be sequentially increased. In addition, the first mode and the second mode may be implemented in various manners of as shown in FIG. 12c, irradiating one pulse of the treatment beam into a plurality of unit pulses having the same output, but sequentially increasing the number of the unit pulses constituting one pulse, or as shown in FIG. 12d, sequentially increasing the magnitude of energy transferred per unit area of the treatment region with a manner of gradually focusing the treatment beam.

As described above, in the aforementioned operation method of the optical treatment apparatus, it has been described that the treatment contents are controlled in the two modes according to the state information about the treatment region, but this is constituted as simple examples for the convenience of description, and according to the patient's lesion contents and the treatment regions, this can be designed in various modifications.

Further, in the present embodiment, the signal detected in the monitoring unit was used for only monitoring the state of the treatment region, but it is also possible to provide a configuration so that the user may directly confirm the state of the RPE cells of the treatment region during treatment, by providing a separate display and displaying a tomographic image of the treatment region on the display.

Glaucoma Lesion Treatment

Glaucoma is a lesion which results in damage to the optic nerve caused by elevation of intraocular pressure, and treatment therefor is performed in such a way that passageways where the intraocular fluid is drained is secured to maintain appropriate intraocular pressure. To this end, by using the optical treatment apparatus according to the present invention, it is possible to improve the drainage characteristics of the fluid by irradiating the trabecular meshwork (TM) tissue, located in the vicinity of the Limbus of the anterior segment, with a treatment beam.

Figure 13:
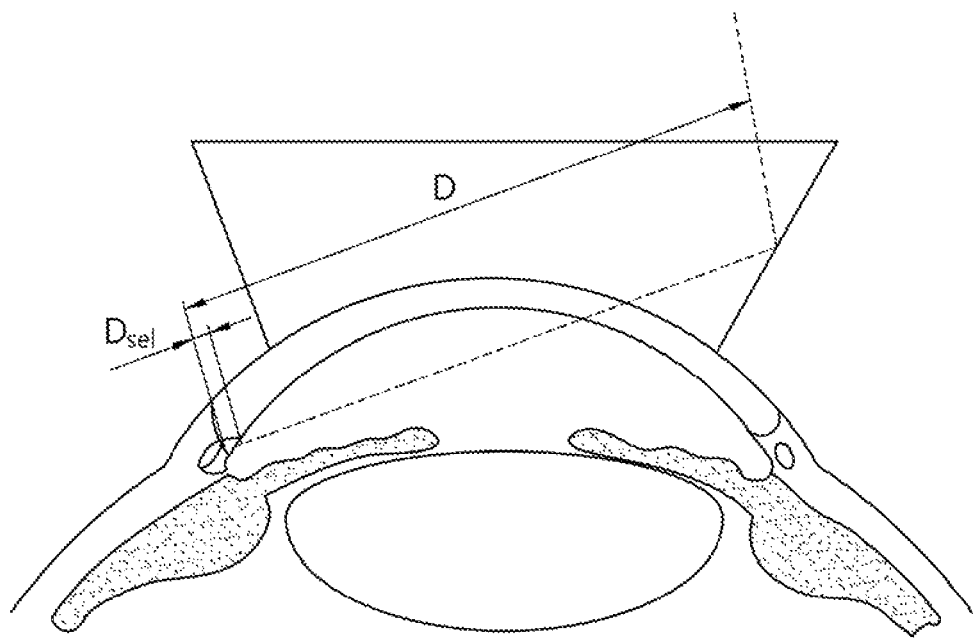
FIG. 13 is a cross-sectional view of the anterior segment in which glaucoma lesion treatment is proceeding.

In order to proceed with such treatment, the optical treatment apparatus is provided with a contact lens (not shown) including a reflector at a position adjacent to the objective lens 600, and the treatment is performed with the patient's eye placed on the contact lens (See FIG. 13).

The treatment beam generation unit 100 may use a treatment beam having light with a wavelength to be absorbed by the melanosomes as in the case of treating the aforementioned retinal lesion. The TM tissue contains pigment components such as the melanosomes as the RPE cells. Accordingly, as the treatment beam is irradiated, energy is transferred to the TM tissue, thereby causing thermal damage to the TM tissue, so that the fluid can be smoothly drained.

While the treatment beam is being irradiated, the monitoring unit 300 irradiates a detection beam and determines the state of the target position in real time based on interference information by the detection beam. At this time, the monitoring unit 300 is configured to extract information corresponding to a depth region of interest among the interference information and determine state information using the extracted information. Here, a depth direction (D in FIG. 13) is a direction in which the treatment beam and the detection beam proceed, and the depth region of interest may be a region where the TM tissue is located (Dsel in FIG. 13).

Since the irradiation method and the monitoring method of the treatment beam are substantially the same as those described in the above-mentioned retinal lesion treatment, the specific device configuration and the driving method are replaced with those described in the retinal lesion treatment.

Skin Lesion Treatment

The optical treatment apparatus described above can also be applied to treat various skin lesions. Treatment for the skin lesions is performed in such a way that a treatment beam is irradiated onto various target positions (for example, hair follicles, melanosomes, collagen layers) to transfer energy depending on the lesion contents.

Then, the monitoring unit 300 senses state information about the treatment region while the treatment is proceeding. Here, a depth region of interest may be a region in which the hair follicles, the melanosomes, collagen, or etc. where the target tissue is located is disposed. Accordingly, the monitoring unit 300 can extract interference information corresponding to the depth region of interest among the interference information by the detection beam, and then use the extracted interference information to determine state information about the treatment region.

Since the irradiation method and the monitoring method of the treatment beam are substantially the same as those described in the above-mentioned retinal lesion treatment, the specific device configuration and the driving method are replaced with those described in the retinal lesion treatment.

So far, although one embodiment of the present invention has been described in detail, the present invention is not limited to the above embodiment, and can be applied to treat various lesions in addition to the above-mentioned embodiment. Also, it should be noted that the present invention can be implemented as various changes and modifications by a person with ordinary skill in the art without departing from of the scope of the technical feature of the invention as defined in the appended claims.

The invention claimed is:

1. An optical treatment apparatus, comprising:
   a treatment beam generation unit for generating a treatment beam;
   a beam delivery unit for forming a path through which the treatment beam generated from the treatment beam generation unit proceeds to a treatment region;
   a monitoring unit for irradiating the treatment region with a plurality of detection beams including first, second, and third detection beams, the first detection beam being irradiated before the second detection beam, the second detection beam being irradiated immediately before the third detection beam, and sensing first, second, and third state information about the treatment region based on first, second, and third interference information, respectively, the first, second, and third interference information being respectively obtained by the first, second, and third detection beams reflected from the treatment region; and
   a control unit for controlling operation of the treatment beam generation unit based on the second and third state information about the treatment region sensed in the monitoring unit,
   wherein the monitoring unit selectively extracts first information about a depth region of interest from the second interference information by the second detection beam, the depth region of interest corresponding to a retinal pigment epithelial (RPE) cell layer, selectively extracts second information about the depth region of interest from the third interference information by the third detection beam, and compares the first information with the second information about the depth region of interest.

2. The apparatus according to claim 1, wherein the monitoring unit determines a state change in the treatment region based on a comparison result of the first information with the second information.

3. The apparatus according to claim 1, wherein each of the first, second, and third interference information is about a region from a surface of the treatment region to a given depth at which a corresponding one of the first, second, and third detection beams reaches.

4. The apparatus according to claim 3, wherein the depth region of interest has a configuration that user may set directly through an interface.

5. The apparatus according to claim 1, wherein based on the second and third interference information obtained by the second and third detection beams, respectively, the monitoring unit senses a temperature change of the treatment region.

6. The apparatus according to claim 1, wherein the monitoring unit detects information about a speckle pattern of each of the first, second, and third detection beam scattered or reflected from the treatment region, thereby sensing each of the first second, and third state information about the treatment region.

7. The apparatus according to claim 6, wherein, when a temperature of the treatment region rises, a volume or a refractive index of tissue located in the treatment region changes, so that characteristics of an optical path through which each of the plurality of detection beams proceeds change, and
wherein the monitoring unit senses a change in the speckle pattern according to the change in the characteristics of the optical path, thereby sensing a state change in the treatment region.

8. The apparatus according to claim 1, wherein the monitoring unit is configured to comprise:
a light source for irradiating the treatment region with the plurality of detection beams;
a detector for detecting the first, second, and third interference information by the first, second, and third detection beams reflected from the treatment region, respectively; and
a processor for determining a state change in the treatment region based on the second and third interference information detected by the detector.

9. The apparatus according to claim 1, wherein the control unit controls the treatment beam generation unit such that energy delivered per unit area of the treatment region gradually increases when a corresponding one of the first, second, and third state information about the treatment region sensed in the monitoring unit is less than a reference value.

10. The apparatus according to claim 1, wherein the monitoring unit includes at least two algorithms for sensing the state of the treatment region, and
generates an error signal in the case a corresponding one of the first, second, and third state information sensed from the respective algorithms has a difference of more than an allowable range.

11. A method of controlling an optical treatment apparatus, the method comprising the steps of:
irradiating a treatment region with a treatment beam by driving a treatment beam generation unit;
irradiating the treatment region, onto which the treatment beam is radiated, with a plurality of detection beams by driving a monitoring unit, the first detection beam being irradiated before the second detection beam, the second detection beam being irradiated immediately before the third detection beam, and sensing first, second, and third state information about the treatment region based on first, second, and third interference information, respectively, the first, second, and third interference information being respectively obtained by the first, second, and third detection beams reflected from the treatment region; and
adjusting, by a control unit, operation of the treatment beam generation unit based on the second and third sensed state information,
wherein the step of sensing the first, second, and third state information about the treatment region comprises:
selectively extracting first information about a depth region of interest from the second interference information by the second detection beam, the depth region of interest corresponding to a retinal pigment epithelial (RPE) cell layer;
selectively extracting second information about the depth region of interest from the third interference information by the third detection beam; and
comparing the first information with the second information about the depth region of interest.

12. The method according to claim 11, wherein the step of sensing the first, second, and third state information about the treatment region further comprises determining a state change in the treatment region based on a comparison result of the first information with the second information.

13. The method according to claim 11, wherein the step of comparing the first information with the second information is performing a cross-correlation calculation of the first information and the second information.

14. The method according to claim 13, wherein the step of sensing the first, second, and third state information about the treatment region further comprises determining a temperature of the treatment region by referring to prestored reference data, thereby determining temperature information about the treatment region corresponding to the calculated value.

15. The method according to claim 14, wherein the step of controlling the operation of the treatment beam generating unit is controlling the treatment beam generating unit such that energy delivered per unit area of the treatment region gradually increases in the case the temperature of the treatment region is less than a predetermined target temperature.

16. The apparatus according to claim 9, wherein the control unit controls the treatment beam generation unit to gradually increase the energy delivered per unit area of the treatment region by gradually focusing the treatment beam.

* * * * *